United States Patent
Masuda

(10) Patent No.: US 9,122,774 B2
(45) Date of Patent: Sep. 1, 2015

(54) MEDICAL IMAGE SYSTEM

(71) Applicant: KONICA MINOLTA, INC., Chiyoda-ku, Tokyo (JP)

(72) Inventor: Ryuuji Masuda, Kunitachi (JP)

(73) Assignee: KONICA MINOLTA, INC., Tokyo (JP)

( * ) Notice: Subject to any disclaimer, the term of this patent is extended or adjusted under 35 U.S.C. 154(b) by 121 days.

(21) Appl. No.: 14/089,511

(22) Filed: Nov. 25, 2013

(65) Prior Publication Data

US 2014/0152692 A1    Jun. 5, 2014

(30) Foreign Application Priority Data

Dec. 5, 2012   (JP) .................................. 2012-265876

(51) Int. Cl.
*G09G 5/00* (2006.01)
*G06F 19/00* (2011.01)

(52) U.S. Cl.
CPC .......... *G06F 19/321* (2013.01); *G06F 19/3406* (2013.01); *G06F 19/3418* (2013.01)

(58) Field of Classification Search
CPC   G06F 19/321; G06F 19/3418; G06F 19/3406
USPC .............................. 345/619; 600/407; 705/2, 3
See application file for complete search history.

(56) References Cited

U.S. PATENT DOCUMENTS

| | | | | |
|---|---|---|---|---|
| 6,003,082 A | * | 12/1999 | Gampper et al. | 709/225 |
| 2002/0111973 A1 | * | 8/2002 | Maddalozzo et al. | 707/526 |
| 2003/0023155 A1 | * | 1/2003 | Tsunoda | 600/407 |
| 2003/0204603 A1 | * | 10/2003 | Buchanan et al. | 709/228 |
| 2004/0069311 A1 | * | 4/2004 | Sasaki et al. | 128/897 |
| 2009/0006421 A1 | * | 1/2009 | Pantos | 707/10 |
| 2009/0164607 A1 | * | 6/2009 | Clark et al. | 709/219 |

FOREIGN PATENT DOCUMENTS

JP    2010-124943 A    6/2010

* cited by examiner

*Primary Examiner* — Jin-Cheng Wang
(74) *Attorney, Agent, or Firm* — Holtz, Holtz, Goodman & Chick PC

(57) ABSTRACT

Disclosed is a medical image system including a medical image management apparatus including a storage unit, a plurality of client terminals and an image generation apparatus. The medical image management apparatus be on standby for import of a medical image when an image import instruction is received from each of the plurality of client terminals, and the medical image management apparatus includes a control unit which stores the medical image in the storage unit and thereafter cancels the standby for image import. In a case where the image import instruction from another client terminal is received, the control unit cancels the standby for image import that is based on the image import instruction from one client terminal when a predetermined condition is fulfilled.

4 Claims, 9 Drawing Sheets

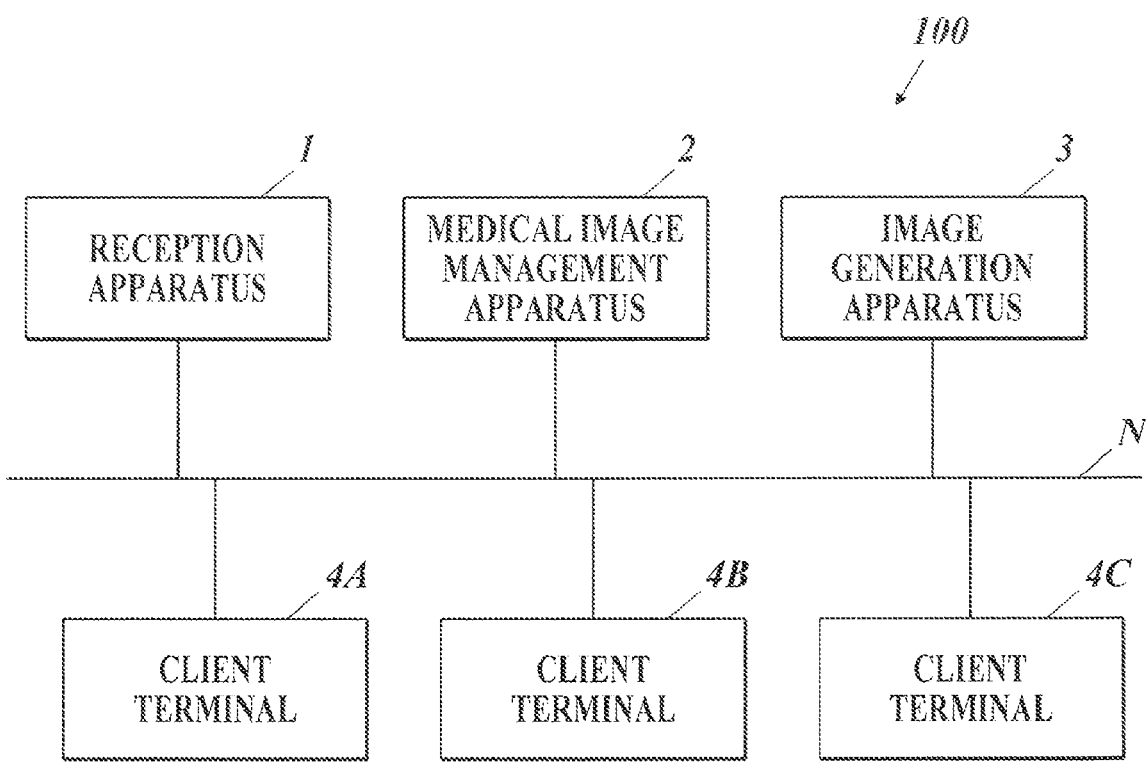

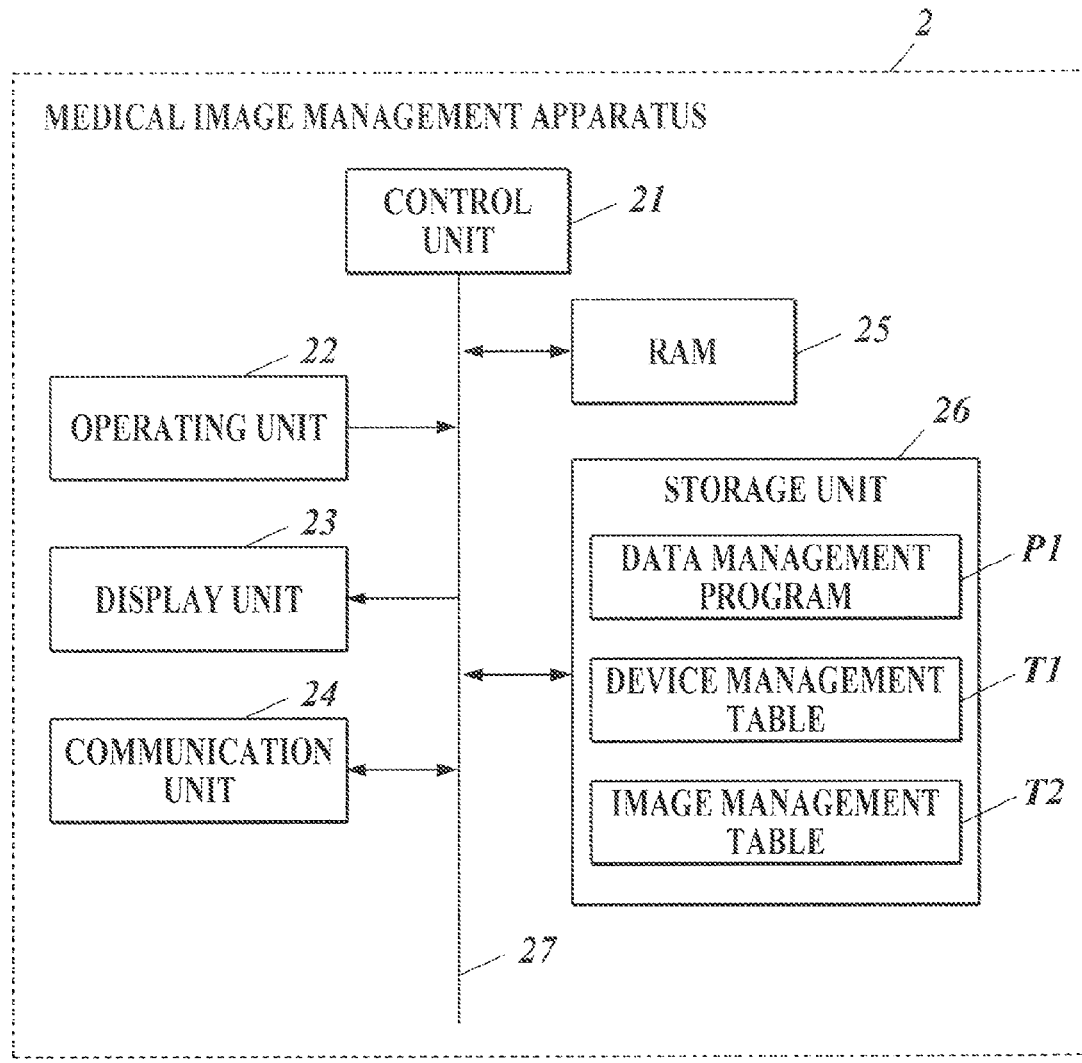

| PATIENT ID | PATIENT NAME | DATE OF IMAGE CAPTURING | FILE PATH |
|---|---|---|---|
|  |  |  |  |
|  |  |  |  |
|  |  |  |  |

T2

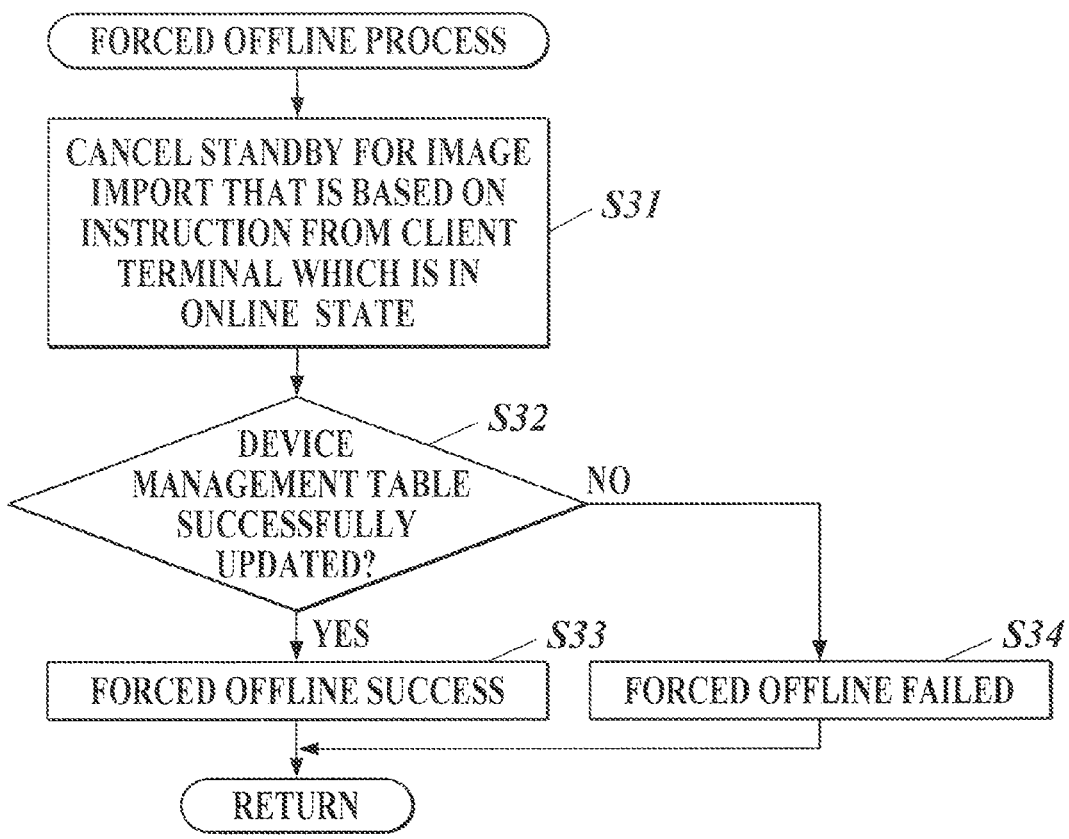

MEDICAL IMAGE SYSTEM

BACKGROUND OF THE INVENTION

1. Field of the Invention

The present invention relates to a medical image system.

2. Description of Related Art

In recent years, medical image management apparatuses which import medical images generated by various types of image generation apparatuses and which store the imported medical images in image DBs (Data Bases) to manage them are used in the medical field (see JP 2010-124943).

In a system including such medical image management apparatus (server apparatus) and client terminals, at a client terminal, logging in to the system is performed in the login screen and a patient who is the target for image capturing is selected among the patients who went through the reception that day in the patient list screen, and then, the screen shifts to the image display screen of the patient who is target for image capturing. When the image import button in the image display screen is pushed, the image generation apparatus corresponding to the image import button and the medical image management apparatus are to be in the online state, and the medical image management apparatus is to be on standby for image import from the image generating apparatus. When image capturing is performed with respect to the patient who is target for image capturing is performed, the medical image generated by the image generation apparatus is imported in to the medical image management apparatus. Then, at the client terminal, a doctor makes a diagnosis on the medical image which is imported in to the medical image management apparatus.

However, in order to prevent mistaking of images, an exclusive control is applied in the medical image management apparatus so as not to accept pushing of the image import button with respect to the image generation apparatus from other client terminals when the image generation apparatus is in the online state according to the instruction (pushing of the image import button) from a certain client terminal. Therefore, there is a problem that the image generation apparatus cannot be used when the image import button is pushed at different client terminals.

Especially, due to mobile terminals, such as tablet type terminals, which perform data communication via wireless LAN (Local Area Network) being used more and more as the client terminals, the possibility that an image be left as-is in a certain client terminal after the image generation apparatus is made to be in the online state is increasing. For example, situations such like bad communication between a client terminal and the medical image management apparatus due to malfunction of the Wi-Fi (Wireless Fidelity) router, the screen returning to the login screen due to session timeout, a user closing the browser, a user taking the client terminal home and the like can be considered.

SUMMARY OF THE INVENTION

In view of the above technical problems, an object of the present invention is to make it possible to import medical images from the image generation apparatuses even if the medical image management apparatus is in standby for image import according to the image import instruction from a different client terminal.

In order to solve the above problems, according to one aspect of the present invention, a medical image system includes a medical image management apparatus including a storage unit, a plurality of client terminals and an image generation apparatus, and the medical image management apparatus and the plurality of client terminals are connected to one another to perform data communication therebetween, the medical image management apparatus and the image generation apparatus are connected to one another to perform data communication therebetween, the medical image management apparatus be on standby for import of a medical image from the image generation apparatus when an image import instruction is received from each of the plurality of client terminals, and the medical image management apparatus includes a control unit which stores the medical image which is sent from the image generation apparatus in the storage unit and cancels the standby for image import, and after the image import instruction is received from one client terminal among the plurality of client terminals and before the standby for image import that is based on the image import instruction from the one client terminal is canceled, in a case where the image import instruction from another client terminal among the plurality of client terminals other than the one client terminal is received, the control unit cancels the standby for image import that is based on the image import instruction from the one client terminal when a predetermined condition is fulfilled.

According to the invention, medical images can be imported from the image generation apparatuses even if the medical image management apparatus is in standby for image import according to the image import instruction from a different client terminal.

Preferably, the predetermined condition is receiving of an instruction to cancel the standby for image import that is based on the image import instruction from the one client terminal from another client terminal.

Preferably, before the standby for image import that is based on the image import instruction from the one client terminal is canceled and when the image import instruction is received from the another client terminal, the control unit notifies the another client terminal that the standby for image import that is based on the image import instruction from the one client terminal is ongoing.

Preferably, the data communication between the medical image management apparatus and the plurality of client terminals is performed in a wireless manner.

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein:

FIG. 1 is a system configuration diagram of a medical image system according to the embodiment of the present invention;

FIG. 2 is a block diagram showing a functional configuration of a medical image management apparatus;

FIG. 3 is an example of a device management table;

FIG. 11 is a flowchart showing a forced offline process.

Figures 4, 5:
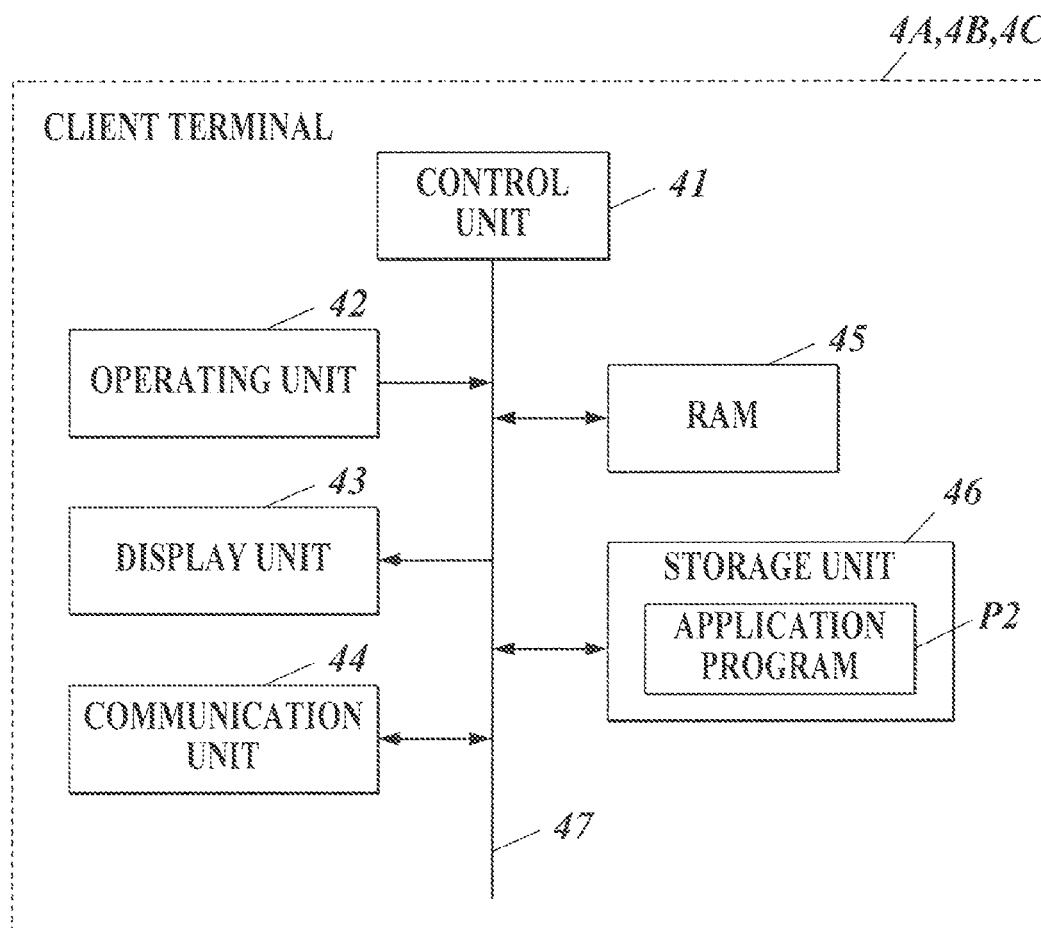
FIG. 4 is an example of an image management table.
FIG. 5 is a block diagram showing a functional configuration of a client terminal.

DESCRIPTION OF THE PREFERRED
EMBODIMENTS

Hereinafter, an embodiment of a medical image system according to the present invention will be described with reference to the drawings. However, the present invention is not limited to the examples shown in the drawings.
[Configuration of Medical Image System]

FIG. 1 shows a system configuration of the medical image system 100. The medical image system 100 includes a reception apparatus 1, a medical image management apparatus 2, an image generation apparatus 3 and a plurality of client terminals 4A, 4B and 4C, for example. Each apparatus which constitutes the medical image system 100 is connected to a communication network N such as LAN via a switching hub (not shown in the drawing), for example. In particular, the medical image management apparatus 2 and the plurality of client terminals 4A, 4B and 4C are connected to one another via the communication network N so that data communication can be carried out therebetween, and the medical image management apparatus 2 and the image generation apparatus 3 are connected to one another via the communication network N so that data communication can be carried out therebetween.

As for the communication method within a hospital, the DICOM (Digital Image and Communication in Medicine) standard is generally used. The DICOM MWM (Modality Worklist Management) or the DICOM MPPS (Modality Performed Procedure Step) is used for communication between the apparatuses which are connected through LAN. Here, the communication method that can be applied to the embodiment is not limited to what is described above.

The reception apparatus 1 is a computer apparatus for carrying out reception and registration of patients who visit the hospital, payment calculation and insurance point calculation, for example. When reception information (reception number, patient's name and the like) is input into the reception apparatus 1, patient information of a patient who went through the reception is stored in the reception apparatus 1 and the reception apparatus 1 provides an external device with patient information of a patient who went through the reception upon a request from the external device.

The medical image management apparatus 2 manages the medical images which are generated in the image generation apparatus 3 in association with the patient information and provides an external device with the medical images and the patient information upon a request from the external device.

The image generation apparatus 3 performs image capturing by setting a body part of a patient who is the target for diagnosis as the subject and generates a medical image by performing digital conversion on the captured image. The image generation apparatus 3 includes a DR (Digital Radiography) apparatus, a CR (Computed Radiography) apparatus and an ultrasound diagnostic apparatus (US), for example. The image generation apparatus 3 attaches patient information (patient ID, patient name, gender, date of birth, age, etc.) and image attribution information (UID, date of image capturing, examination ID, examined part, etc.) to medical images.

Each of the client terminals 4A, 4B and 4C is a computer apparatus for giving instructions regarding importing of medical images from the image generation apparatus 3 in the medical image management apparatus 2 and viewing of medical images managed by the medical image management apparatus 2. Each of the client terminals 4A, 4B and 4C is configured with a tablet type terminal or the like, and data communication between each of the client terminals 4A, 4B and 4C and the medical image management apparatus 2 is performed in a wireless manner.

FIG. 2 shows a functional configuration of the medical image management apparatus 2. As shown in FIG. 2, the medical image management apparatus 2 includes a control unit 21, an operating unit 22, a display unit 23, a communication unit 24, a RAM (Random Access Memory) 25 and a storage unit 26, for example. These units are connected to one another by a bus 27.

The control unit 21 is configured with a CPU (Central Processing Unit), for example. The control unit 21 reads out various types of programs such as a system program and processing programs which are stored in the storage unit 26 and opens them in the RAM 25 to execute various types of processing according to the opened programs.

The operating unit 22 is configured by including a key board including character input keys, number input keys and various function keys, for example, and a pointing device such as a mouse. The operating unit 22 outputs push signals of the keys in the key board that are pushed and operation signals of the mouse to the control unit 21 as input signals.

The display unit 23 is configured with a LCD (Liquid Crystal Display), for example. The display unit 23 displays various types of screens according to the instructions of display signals which are input from the control unit 21.

The communication unit 24 is configured with a network interface, for example. The communication unit 24 performs sending and receiving of data with an external device which is connected to the communication network N.

The RAM 25 functions as a work area for temporarily storing various types of programs read out from the storage unit 26 that can be executed by the control unit 21, input and output data and the like in various processing which are executed and controlled by the control unit 21.

The storage unit 26 is configured with a HDD (Hard Disk Drive) memory or a non-volatile memory such as a semiconductor memory, etc. In the storage unit 26, various programs, data necessary for various processing and the like are stored. For example, in the storage unit 26, the data management program P1, the device management table T1, the image management table T2, medical images and the like are stored.

FIG. 3 shows an example of the device management table T1. The device management table T1 is a table for managing the information regarding the client terminal 4A, 4B or 4C which gave the image import instruction. In the device management table T1, "client terminal name" and "patient ID" are stored so as to be associated to each other.

In the field of "client terminal name", the client terminal name (for example, IP address) of the client terminal 4A, 4B or 4C which gave the image import instruction is stored.

In the field of "patient ID", the patient ID of a patient who is the target for image capturing is stored.

FIG. 4 shows an example of the image management table T2. The image management table T2 is a table for managing information regarding medical images. In the image management table T2, "patient ID", "patient name", "date of image capturing", "file path", for example, are stored as one record by being associated to one another.

For each record, in the field of "patient ID", the patient ID of a patient who is the target for image capturing is stored.

For each record, in the field of "patient name", the patient name (Ascii, Kana characters, Kanji characters) of the patient who is the target for image capturing is stored.

For each record, in the field of "date of image capturing", the date when the subject image was captured is stored.

For each record, in the field of "file path", the file path indicating the storage place of the file of the subject image is stored.

When the control unit 21 receives the image import instruction from each of the client terminals 4A, 4B and 4C, the control unit 21 makes the medical image management apparatus 2 be in a standby for importing medical images from the image generation apparatus 3. In particular, when any one of client terminals 4A, 4B and 4C gives the image import instruction, the control unit 21 stores the client terminal name of the client terminal which gave the image import instruction in the field of "client terminal name" in the device management table T1 and stores the patient ID of the patient who is the target for image capturing in the field of "patient ID" in the device management table T1. Here, the medical image management apparatus 2 can accept the image import instruction only when the field of "client terminal name" and the field of "patient ID" in the device management table T1 are "NULL".

The control unit 21 stored the medical image (s) sent from the image generation apparatus 3 according to the image import instruction from each of the client terminals 4A, 4B and 4C in the storage unit 26. Thereafter, the control unit 21 cancels the standby for image import that is according to the image import instruction from the client terminals 4A, 4B and 4C. In particular, the control unit 21 returns the field of "client terminal name" and the field of "patient ID" in the device management table T1 to "NULL".

The control unit 21 provides the client terminals 4A, 4B or 4C, which gave the image import instruction, with the medical image(s) stored in the storage unit 26.

In a case where the control unit 21 receives the image import instruction from another client terminal in the plurality of client terminals 4A, 4B and 4C other than one client terminal after the image import instruction is received from the one client terminal among the plurality of client terminals 4A, 4B and 4C and before the standby for image import that is based on the image import instruction from the one client terminal is canceled, the control unit 21 cancels the standby for image import that is based on the image import instruction from the one client terminal if a predetermined condition is fulfilled.

In particular, in a case where the control unit 21 receives the image import instruction from another client terminal before the standby for image import that is based on the image import instruction from one client terminal is canceled, the control unit 21 notifies to the another client terminal that the standby for image import that is based on the image import instruction from the one client terminal is ongoing.

Then, if the control unit 21 receives the instruction to cancel the standby for image import that is based on the image import instruction from the one client terminal from another client terminal (if a predetermined condition is fulfilled), the control unit 21 cancels the standby for image import that is based on the image import instruction from the one client terminal.

FIG. 5 shows a functional configuration of each of the client terminals 4A, 4B and 4C. As shown in FIG. 5, each of the client terminals 4A, 4B and 4C includes a control unit 41, an operating unit 42, a display unit 43, a communication unit 44, a RAM 45 and a storage unit 46, for example. These units are connected to one another by a bus 47.

The control unit 41 is configured with a CPU or the like. The control unit 41 reads out various programs such as a system program and processing programs which are stored in the storage unit 46, opens the programs in the RAM 45 and executes various processes according to the programs that are opened.

The operating unit 42 includes a key board having character input keys, number input keys, various function keys and such like and a pointing device such as a mouse. The operating unit 42 outputs pushing signals of the keys which are pushed in the key board and operation signals of the mouse to the control unit 41 as input signals.

In a case where the client terminals 4A, 4B and 4C are tablet type terminals, the operating unit 42 includes operation keys such as a power key to turn the power on/off and a touch panel which is layered on the display unit 43, and the operating unit 42 outputs operation signals corresponding to various operation keys and operation signals according to the positions where a user touched and operated with his/her finger or the like to the control unit 41.

The display unit 43 is configured with a LCD. The display unit 43 displays various types of screens according to the instructions of display signals which are input from the control unit 41.

The communication unit 44 is configured with a network interface, for example. The communication unit 44 performs sending and receiving of data with an external device which is connected to the communication network N.

The communication unit 44 may be a unit which performs sending and receiving of data through wireless communication such as WI-FI communication, for example, with an external device connected to the communication network N. For example, the communication unit 44 can be realized by an antenna or a RF converter, for example, which performs sending and receiving of wireless signals via a wireless communication base station established by a communication service provider. The communication unit 44 may be a unit that performs wireless communication with the medical image management apparatus 2 by using an infrared data communication (IrDA/IrMC), Bluetooth (registered trademark) or the like.

The RAM 45 functions as a work area for temporarily storing various types of programs read from the storage unit 46 that can be executed by the control unit 41, input and output data and the like in various processing which are executed and controlled by the control unit 41.

The storage unit 46 is configured with a HDD (Hard Disk Drive) memory or a non-volatile memory such as a semiconductor memory, etc. In the storage unit 46, various types of programs, data necessary for various processes and the like are stored. For example, in the storage unit 46, the application program P2 is stored.

[Operation of Medical Image System]

Next, operation in the medical image system 100 will be described.

Figure 6:
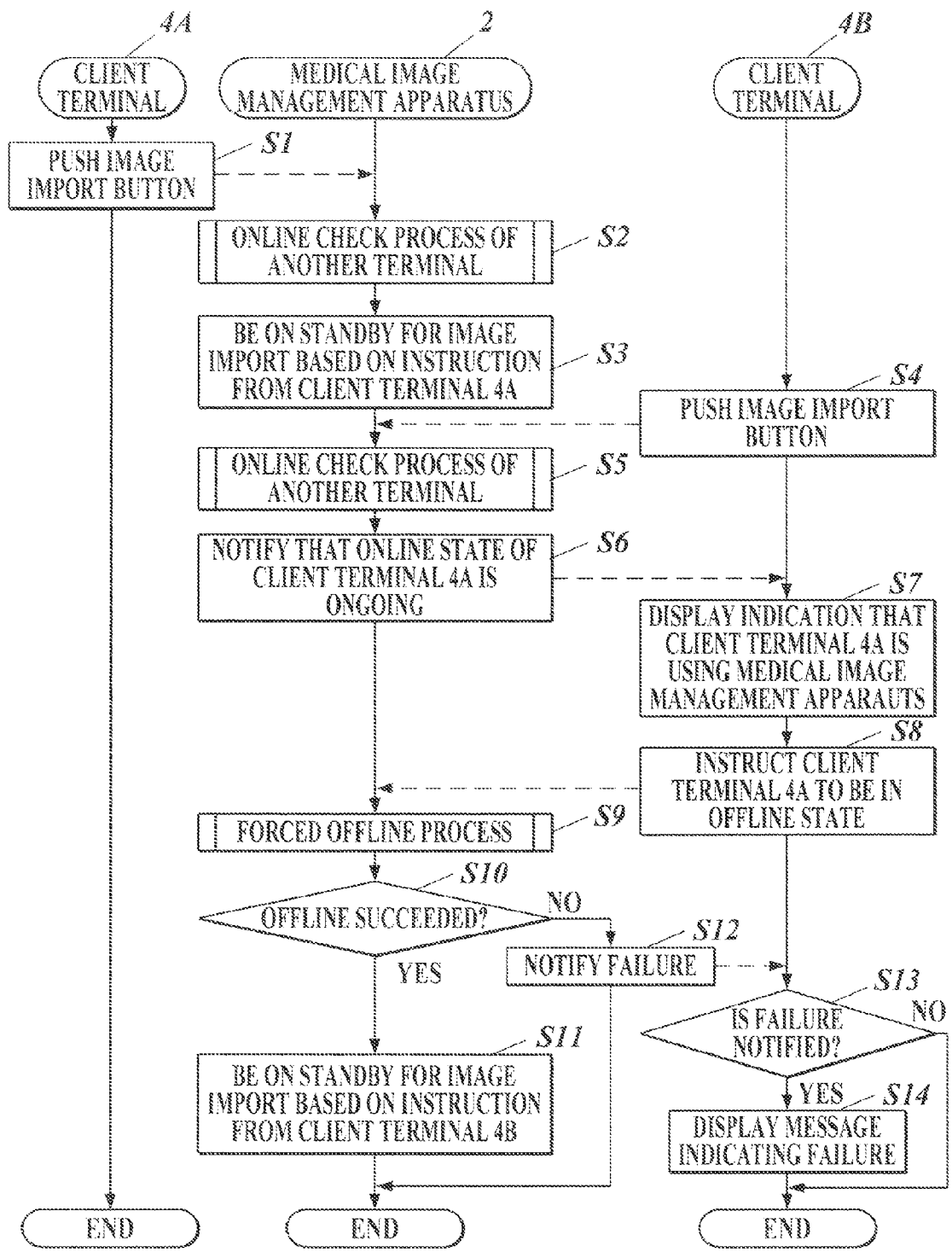
FIG. 6 is a ladder chart showing a forced cancelling process performed in the medical image system.

FIG. 6 is a ladder chart showing the forced canceling process performed in the medical image system 100. Processes performed in the medical image management apparatus 2 are realized by software processing where the control unit 21 and the data management program P1 stored in the storage unit 26 cooperate with each other. Processes performed in the client terminals 4A and 4B are realized by software processing where the control unit 41 and the application program P2 stored in the storage unit 46 cooperate with each other.

At the start of this process, it is assumed that the medical image management apparatus 2 has not received image import instructions from the client terminals 4A, 4B and 4C.

In the client terminal 4A, the control unit 41 obtains patient information of patients who went through the reception process that day from the reception apparatus 1 and displays the patient list screen according to the obtained patient information in the display unit 43. When a patient who is the target for image capturing is selected among the patients displayed in the patient list screen through operation of the operating unit 42, the control unit 41 displays the image display screen for displaying an image of the patient who is the target for image capturing in the display unit 43.

Figure 7:
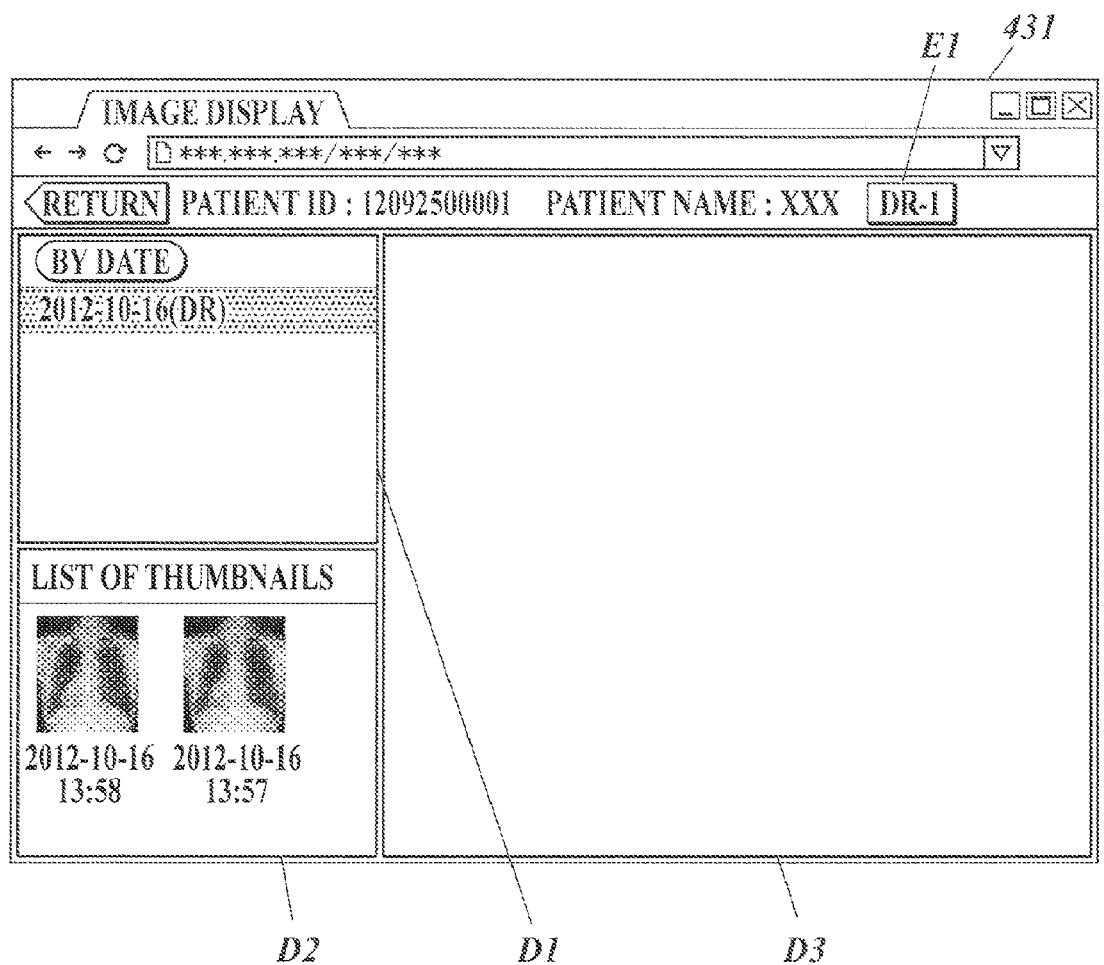
FIG. 7 is an example of an image display screen.

FIG. 7 shows an example of the image display screen 431 of the patient having the patient name XXX displayed in the display unit 43 at the client terminal 4A. The image display screen 431 includes the examination list display section D1, the thumbnail image display section D2, the image display section D3 and the image import button E1. In the examination list display section D1, a list of examinations (captured images) performed on a patient in the past is displayed. In the thumbnail image display section D2, thumbnail images of the images captured in the examination which is selected in the examination list display section D1 are displayed. In the image display section D3, a medical image which is instructed to be imported by the client terminal 4A or a diagnosis target image which is selected among the thumbnail images displayed in the thumbnail image display section D2 is to be displayed. Images are not displayed in the image display section D3 before image(s) is imported or before a diagnosis target image is selected. The image import button E1 is provided for each image generation apparatus 3 and is a button for instructing import of a medical image(s) sent from the corresponding image generation apparatus 3 as an image (s) of the patient who is currently target for diagnosis.

In the client terminal 4A, if the image import button E1 corresponding to the image generation apparatus 3 which performed image capturing is pushed through an operation of the operating unit 42 in a state where the image display screen 431 is displayed in the display unit 43 (step S1), the control unit 41 sends an instruction (image import instruction) to import a medical image sent from the image generation apparatus 3 corresponding to the pushed image import button E1 as an image of the target patient to the medical image management apparatus 2 via the communication unit 44. In particular, the control unit 41 sends the client terminal name (IP address) of the client terminal 4A and the patient ID of the patient who is the target for image capturing to the medical image management apparatus 2 via the communication unit 44.

In the medical image management apparatus 2, when the communication unit 24 receives the image import instruction, the control unit 21 performed the online check process of another terminal (step S2).

Figure 8:
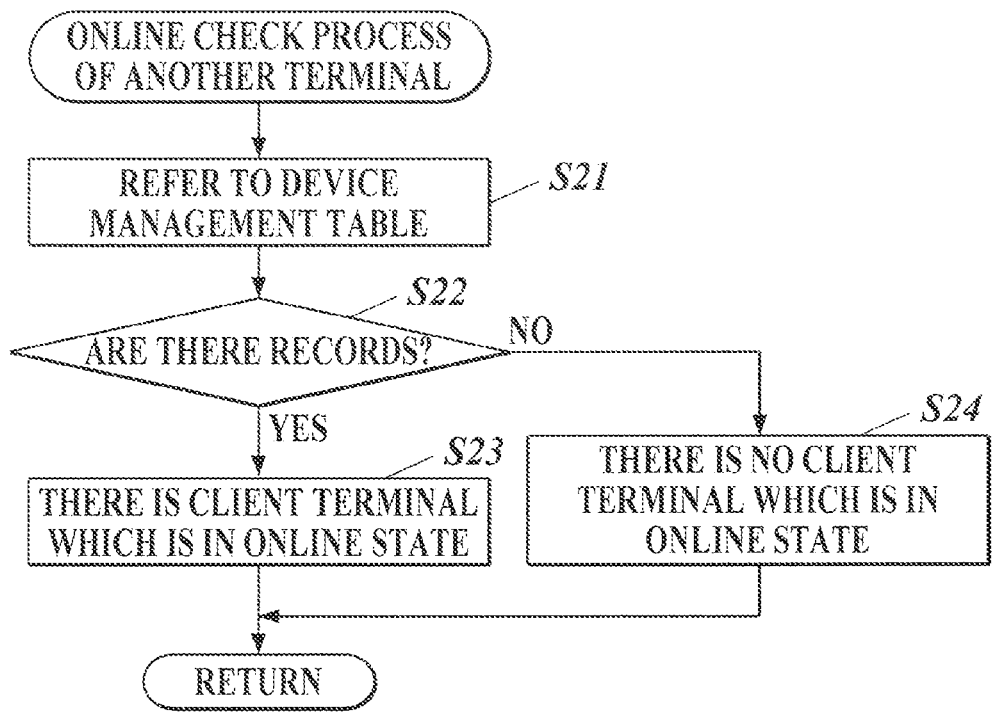
FIG. 8 is a flowchart showing an online check process of another terminal.

Here, the online check process of another terminal will be described with reference to FIG. 8.

The control unit 21 refers to the device management table T1 stored in the storage unit 26 (step S21) and determines whether there are records in the field of "client terminal name" and the field of "patient ID" (step S22).

If there are records in the field of "client terminal name" and the field of "patient ID" in the device management table T1 (step S22; YES), the control unit 21 determines that there is a client terminal which is in the online state (step S23) and determines that the medical image management apparatus 2 in on standby for image import that is based on the image import instruction from the client terminals 4A, 4B or 4C which corresponds to the client terminal name stored in the field of "client terminal name".

On the other hand, if there is no record ("NULL") in the field of "client terminal name" and the field of "patient ID" in the device management table T1 (step S22; NO), the control unit 21 determines that there is no client terminal which is in the online state (step S24).

After step S23 of step S24, the online check process of another terminal ends.

In step S2 in FIG. 6, it is determined that there is no client terminal which is in the online state. The control unit 21 stores the client terminal name of the client terminal 4A, which gave the image import instruction, in the field of "client terminal name" in the device management table T1 stored in the storage unit 26 and the patient ID of the patient who is selected at the client terminal 4A in the field of "patient ID" in the device management table T1, and the medical image management apparatus 2 is to be on standby for importing an image generated in the image generation apparatus 3 (step S3). That is, the medical image management apparatus 2 is to be on standby for image import based on the image import instruction from the client terminal 4A.

Hereafter, image capturing of the patient may not be performed in the image generation apparatus due to certain reasons such as cutoff of Wi-Fi communication, breakdown of a router, a user taking home the client terminal 4A or losing it, session timeout and the like.

In such condition, in the client terminal 4B, the control unit 41 obtains patient information of patients who went through the reception process on that day from the reception apparatus 1 and displays the patient list screen according to the obtained patient information in the display unit 43. When a patient who is the target for image capturing is selected among the patients displayed in the patient list screen through operation of the operating unit 42, the control unit 41 displays the image display screen for displaying an image of the patient who is the target for image capturing in the display unit 43.

When the image import button corresponding to the image generation apparatus 3 which performs image capturing is pushed at the client terminal 4B through operation of the operating unit 41 in a state where the image display screen is displayed in the display unit 43 (step S4), the control unit 41 sends an instruction (image import instruction) to import a medical image sent from the image generation apparatus 3 corresponding to the pushed image import button as an image of the target patient to the medical image management apparatus 2 via the communication unit 44. In particular, the control unit 41 sends the client terminal name (IP address) of the client terminal 4B and the patient ID of the patient who is the target for image capturing to the medical image management apparatus 2 via the communication unit 44.

In the medical image management apparatus 2, when the communication unit 24 receives the image import instruction, the control unit 21 performs the online check process of another terminal (see FIG. 8) (step S5).

In step S5 of FIG. 6, because the medical image management apparatus 2 is already on standby for image import that is based on the image import instruction from the client terminal 4A, it is determined that there is a client terminal which is in the online state. Then, the control unit 21 notifies the client terminal 4B of information indicating that the online state of the client terminal 4A is ongoing (that the medical image management apparatus 2 continues to be on standby for image import that is based on the image import instruction from the client terminal 4A) via the communication unit 24 (step S6).

In the client terminal 4B, the communication unit 44 receives the information indicating that the online state of the client terminal 4A is ongoing and the control unit 41 displays a notification indicating that the client terminal 4A is using the medical image management apparatus 2 in the display unit 43 (step S7). In such way, a user of the client terminal 4B can know that the medical image management apparatus 2 is on standby for image import that is based on the image import instruction from the client terminal 4A.

Figure 9:
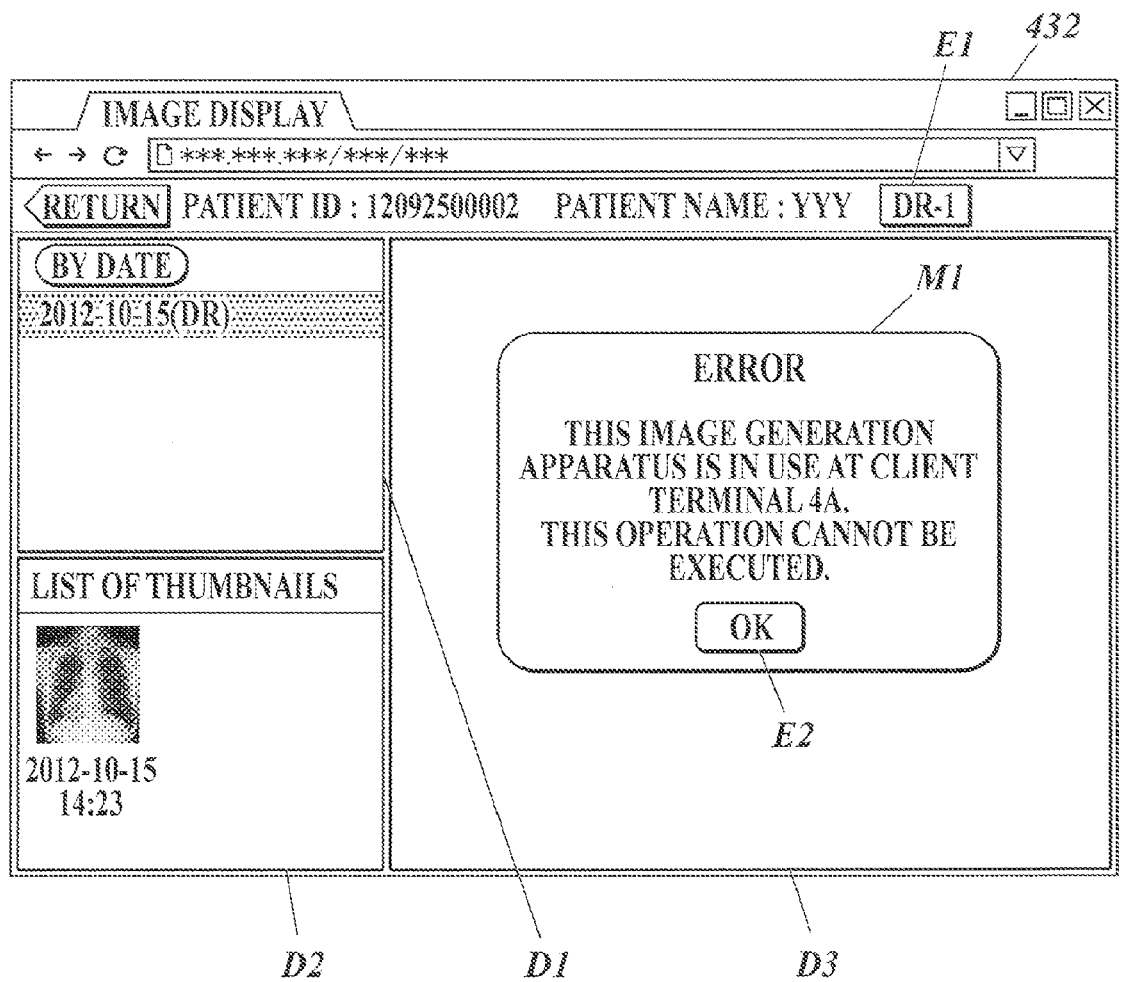
FIG. 9 is an example of an image display screen including a message dialog notifying the online state of another terminal.

FIG. 9 shows an example of the image display screen 432 of the patient having the patient name YYY displayed in the display unit 43 at the client terminal 4B. The configuration of the image display screen 432 is the same as the image display screen 431 shown in FIG. 7. Therefore, its description is omitted. When the image import button E1 is pushed in the image display screen 432 through operation of the operating unit 42, the message dialog M1 is displayed in the display unit 43. The message dialog M1 includes a message such as "This image generation apparatus is in use at the client terminal 4A. This operation cannot be executed.", for example.

Figure 10:
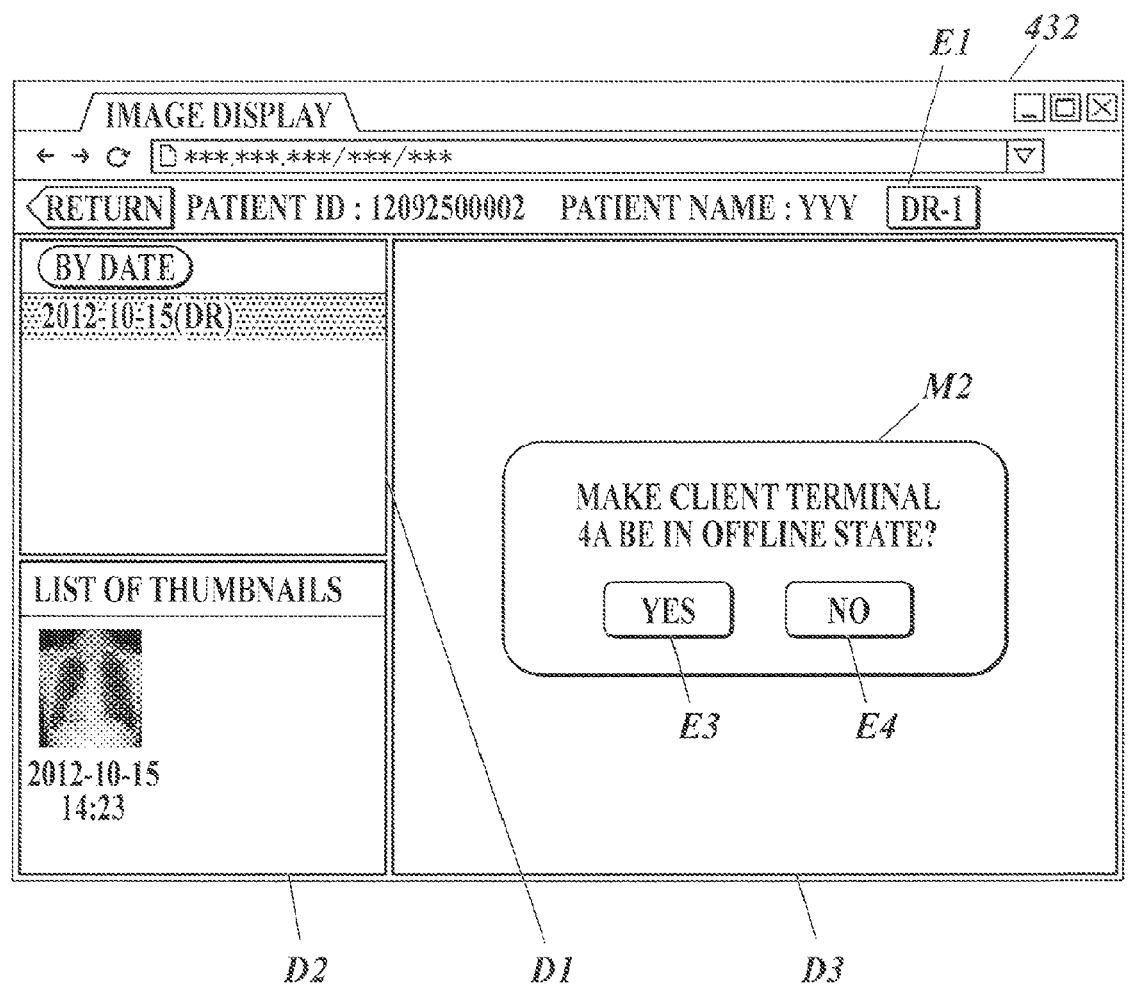
FIG. 10 is an example of an image display screen including a message dialog for selecting canceling of the online state of another terminal.

When the OK button E2 included in the message dialog M1 is pushed through operation of the operation unit 42 at the client terminal 4B, the message dialog M2 shown in FIG. 10 is shown in the display unit 43. The message dialog M2 includes a message such as "Make the client terminal 4A be in offline state?", for example. The message dialog M2 includes the YES button E3 and the NO button E4. The YES button E3 is a button for instructing to cancel the online state (the standby for image import that is based on the image import instruction from the client terminal 4A) of the client terminal 4A. The NO button E4 is a button for instructing to continue the online state of the client terminal 4A.

When the YES button E3 is pushed through operation of the operating unit 42 at the client terminal 4B, the control unit 41 sends an instruction to cancel the online state of the client terminal 4A to the medical image management apparatus 2 via the communication unit 44 (step S8).

When the communication unit 24 receives the instruction to cancel the online state of the client terminal 4A (the instruction to cancel the standby for image import that is based on the image import instruction from the client terminal 4A) in the medical image management apparatus 2, the control unit 21 performs the forced offline process (step S9).

The forced offline process will be described with reference to FIG. 11.

The control unit 21 cancels the standby for image import that is based on the image import instruction from the client terminal which is in the online state (step S31). In particular, the control unit 21 changes the field of "client terminal name" and the field of "patient ID" in the device management table T1 stored in the storage unit 26 to "NULL".

Next, the control unit 21 determines whether updating of the device management table T1 succeeded (step S32). If the updating of the device management table T1 succeeded (step S32; YES), the control unit 21 determines that the forced offline succeeded (step S33).

On the other hand, if the updating of the device management table T1 failed (step S32; NO), the control unit 21 determines that the forced offline failed (step S34).

After step S33 or step S34, the forced offline process ends.

Returning to FIG. 6, if the offline succeeded (step S10; YES), in the medical image management apparatus 2, the control unit 21 stores the client terminal name of the client terminal 4B, which gave the image import instruction, in the field of "client terminal name" in the device management table T1 stored in the storage unit 26 and stores the patient ID of the patient selected at the client terminal 4B in the field of "patient ID" in the device management table T1, and the medical image management apparatus 2 is to be on standby for importing an image generated in the image generation apparatus 3 (step S11). That is, the medical image management apparatus 2 is to be on standby for image import that is based on the image import instruction from the client terminal 4B.

If the offline failed in step S10 (step S10; NO), the control unit 21 sends a notification indicating that the offline failed to the client terminal 4B via the communication unit 24 (step S12).

In the client terminal 4B, the control unit 41 determines whether the notification indicating that the offline failed is received via the communication unit 44 (step S13). If the notification indicating that the offline failed is received (step S13; YES), the control unit 41 displays a message indicating that the offline failed in the display unit 43 (step S14).

If the notification indicating that the offline failed is not received in step S13 (step S13; NO), the process ends here.

As described above, according to the embodiment, even if the medical image management apparatus 2 is on standby for image import based on the image import instruction from another client terminal, a medical image can be imported from the image generation apparatus 3 because the standby for image import can be canceled.

Further, the client terminal which gave the image import instruction later is informed of the medical image management apparatus 2 being on standby for image import based on the image import instruction from another client terminal. Therefore, a user of the client terminal which gave the image import instruction later can know that the medical image management apparatus 2 is on standby for image import based on the image import instruction from another client terminal.

Moreover, based on the instruction to cancel the standby for image import received from the client terminal which gave the image import instruction later, the standby for image import based on the image import instruction from the client terminal which gave the image import instruction first can be canceled.

Conventionally, the medical image management apparatus 2 and the client terminals 4A, 4B and 4C are connected through wired connection in many cases. Therefore, there were very little problems such as the connection being cutoff in the middle of communication or the client terminals 4A, 4B and 4C missing. In contrary, in recent years, because mobile terminals using wireless communication are more and more being used as the client terminals 4A, 4B and 4C, there is a great possibility that the communication be unstable and the client terminals 4A, 4B and 4C being moved around. Therefore, the present invention exhibits greater advantage in systems using wireless communication.

The above embodiment is an example of a medical image system according to the present invention, and the present invention is not limited to the above embodiment. Detail configurations and detail operation of the apparatuses constituting the system can be changed arbitrarily within the scope of the invention.

For example, the client terminal name of the client terminal which gave the image import instruction may be managed with information indicating whether the client terminal is a mobile terminal or not attached thereto as the "client terminal name" in the device management table T1 (for example, attach the letter string "mobile" if the client terminal is a mobile terminal, etc.), and the forced offline process can be performed only when the client terminal which gave the image import instruction first is a mobile terminal.

Further, the above embodiment describes a case where, if there are a plurality of image generation apparatuses 3, the medical image management apparatus 2 cannot be in on standby for image import with respect to other image generation apparatuses 3 if the medical image management apparatus 2 is already on standby for image import with respect to any one of the image generation apparatuses 3. However, the standby for image import state of the medical image management apparatus 2 may be managed with respect to each image generation apparatus 3.

Furthermore, in the above embodiment, description is given for a case where "a predetermined condition" for canceling the standby for image import based on the image import instruction from the client terminal which gave the image import instruction first is receiving of the instruction indicating to cancel the standby for image import from another client terminal. However, the standby for image import may be canceled in the medical image management apparatus 2 according to a condition such as a predetermined time period elapsing since the image import instruction from the client terminal which gave the image import instruction first was received or detecting that the communication with the client terminal which gave the image import instruction first being cutoff.

In the above description, an example where HDD or a non-volatile memory is used as a computer readable medium in which program for executing various processes are stored is shown. However, the computer readable medium is not limited to such example. As other computer readable medium, a portable recording mediums such as CD-ROM, for example, can be used. Further, carrier wave may be applied as a medium for providing data of programs through a communication circuit.

The entire disclosure of Japanese Patent Application No. 2012-265876 filed on Dec. 5, 2012 is incorporate herein by reference in its entirety.

What is claimed is:

1. A medical image system, comprising:
a medical image management apparatus including a storage unit;
a plurality of client terminals; and
an image generation apparatus,
wherein
the medical image management apparatus and the plurality of client terminals are connected to one another to perform data communication therebetween,
the medical image management apparatus and the image generation apparatus are connected to one another to perform data communication therebetween,
the medical image management apparatus be on standby for import of a medical image from the image generation apparatus when an image import instruction is received from each of the plurality of client terminals, and the medical image management apparatus includes a control unit which stores the medical image which is sent from the image generation apparatus in the storage unit and thereafter cancels the standby for image import, and
after the image import instruction is received from one client terminal among the plurality of client terminals and before the standby for image import that is based on the image import instruction from the one client terminal is canceled, in a case where the image import instruction from another client terminal among the plurality of client terminals other than the one client terminal is received, the control unit cancels the standby for image import that is based on the image import instruction from the one client terminal when a predetermined condition is fulfilled.

2. The medical image system of claim 1, wherein the predetermined condition is receiving of an instruction to cancel the standby for image import that is based on the image import instruction from the one client terminal from another client terminal.

3. The medical image system of claim 1, wherein before the standby for image import that is based on the image import instruction from the one client terminal is canceled and when the image import instruction is received from the another client terminal, the control unit notifies the another client terminal that the standby for image import that is based on the image import instruction from the one client terminal is ongoing.

4. The medical image system of claim 1, wherein the data communication between the medical image management apparatus and the plurality of client terminals is performed in a wireless manner.

* * * * *